United States Patent [19]

Findlay et al.

[11] Patent Number: 4,657,918
[45] Date of Patent: Apr. 14, 1987

[54] 3-[6-[3-PYRROLIDINO-1-(4-TOLYL)PROP-1E-ENYL]-2-PYRIDYL]PROPIONIC ACID AND DERIVATIVES HAVING ANTI-HISTAMINIC ACTIVITY

[75] Inventors: John W. A. Findlay, Chapel Hill, N.C.; Geoffrey G. Coker, Bromley, England

[73] Assignee: Burroughs Wellcome Co., Research Triangle Park, N.C.

[21] Appl. No.: 779,877

[22] Filed: Sep. 25, 1985

Related U.S. Application Data

[62] Division of Ser. No. 462,874, Feb. 1, 1983, Pat. No. 4,562,258.

[30] Foreign Application Priority Data

Feb. 4, 1982 [GB] United Kingdom ............... 8203261

[51] Int. Cl.$^4$ .................. C07D 401/06; A61K 31/44; A61K 31/435
[52] U.S. Cl. ..................................... 514/318; 514/336; 514/343; 514/357; 546/194; 546/281; 546/268; 546/333
[58] Field of Search ............... 546/281, 184, 268, 333; 514/336, 318, 343, 357

[56] References Cited

FOREIGN PATENT DOCUMENTS 2114565 8/1983 United Kingdom ............... 514/343

Primary Examiner—Alan L. Rotman
Attorney, Agent, or Firm—Donald Brown

[57] ABSTRACT

This disclosure describes compounds of Formula I.

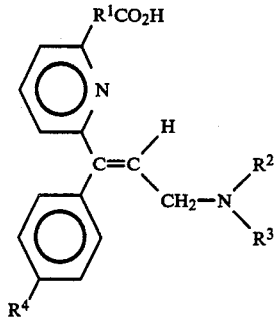

(including their pharmaceutically acceptable salts and esters) which have potent antihistamine activity which are substantially free from sedative effects.

7 Claims, No Drawings

3-[6-[3-PYRROLIDINO-1-(4-TOLYL)PROP-1E-ENYL]-2-PYRIDYL]PROPIONIC ACID AND DERIVATIVES HAVING ANTI-HISTAMINIC ACTIVITY

This is a division of application Ser. No. 462,874 filed Feb. 1, 1983, now U.S. Pat. No. 4,562,258 issued Dec. 31, 1985.

The present invention relates to new chemical compounds exhibiting antihistamine activity, to processes for preparing them, to novel intermediates involved in their preparation, to pharmaceutical compositions containing them and to their use in medicine.

U.S. Pat. No. 2,717,023 discloses a group of pyridyl propenylamines with antihistamine activity, the most outstanding of which is the compound named (E)-1-(4-methylphenyl)-1-(2-pyridyl)-3-pyrrolidinoprop-1-ene and hereinafter referred to by its generic name, triprolidine. Triprolidine has gained widespread clinical acceptance and is one of the most potent antihistamines available.

The antihistamines now in use, eg. diphenhydramine, the pheniramines, pyrilamine, promethazine and triprolidine may cause sedation or drowsiness in some patients.

A novel group of compounds having antihistamine activity has now been discovered. These compounds have been found to be substantially free from sedative effects and have little or no anticholinergic effects.

Accordingly this invention provides the compounds of formula I.

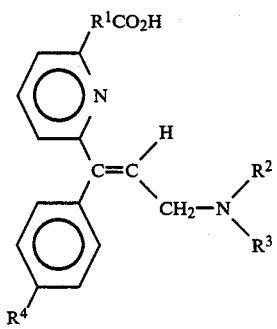

or corresponding straight and branched lower alkyl (1-4 carbon atoms) esters and salts thereof; wherein $R^1$ is $(CH_2)_n$, n is an integer 0 to 7, or $(CH_2)_aCH=CH-(CH_2)_b$, a and b are independently 0 to 5 and the sum of a and b does not exceed 5; $R^2$ and $R^3$ are the same or different and can be hydrogen, $C_{1-4}$ alkyl or taken together with the nitrogen comprise a nitrogen containing heterocyclic ring having four to six ring members; $R^4$ is hydrogen, halogen, $C_{1-4}$ alkoxy or $C_{1-4}$ alkyl optionally substituted by one to three halogen atoms; provided that when $R^1$ is —CH=CH— and $NR^2R^3$ is pyrrolidine, $R^4$ is not —$CH_3$ or —$CF_3$.

If the carboxylic acid side chain is placed in any position on the pyridine ring other than that shown in formula 1 (i.e., the 2 position) or the configuration about the central double bond (from the carbon bonded to the pyridine and phenyl rings) is Z rather than E as shown above, the antihistaminic activity of such a compound is significantly reduced. That is, its antihistaminic activity is below the point of practical value.

Esters of the compounds of the formula (I) are also useful intermediates in the preparation of the parent compounds of the formula (I). Salts of the compounds of the formula (I) may be either acid addition salts or salts formed with the carboxylic acid group. Pharmaceutically acceptable salts are preferred.

Preferred compounds of the formula (I) include:

Compound
A    3-{6-[3-Pyrrolidino-1-(4-tolyl)prop-1E-enyl]-2-pyridyl}propionic acid
B    (E)-3-{6-[3-Dimethylamino-1-(4-tolyl)prop-1E-enyl]-2-pyridyl}acrylic acid
C    (E)-3-{6-[3-pyrrolidino-1-(4-methoxyphenyl)prop-1E-enyl]-2-pyridyl}acrylic acid
D    (E)-3-{6-[1-(4-chlorophenyl)-3-pyrrolidinoprop-1E-enyl]-2-pyridyl}acrylic acid
E    (E)-3-[6-(1-phenyl-3-pyrrolidinoprop-1E-enyl)-2-pyridyl]acrylic acid
F    6-[3-pyrrolidino-1-(4-tolyl)prop-1E-enyl]pyridine-2-carboxylic acid 1. A method for preparing compounds of formula (I) comprises reacting a compound of (II) with a compound of formula (III) by the Wittig method (see *Organic Reactions*, 14, 270–490 (1965) and *Pure and Applied Chemistry*, 9, 245–254 (1964)).

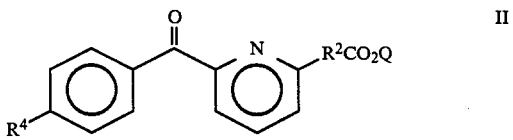

wherein $R^1$, $R^2$, $R^3$ and $R^4$ are the same as defined for formula (I), $R^5$ is aryl such as phenyl or lower alkyl (1 to 4 carbons) and Q is a lower alkyl group (1–4 carbons) or an alkali metal such as lithium or sodium. The reaction may be followed by deprotection of the carboxyl group as necessary. The product may be converted to an acid addition salt, a salt of the carboxylic acid, or an ester by conventional methods.

The compound of formula (III) is a Wittig reagent which may be prepared by treatment of a phosphonium salt (IV) with a strong base, for example an alkyl or aryl lithium compound or sodium hydride in a suitable solvent, for example toluene or tetrahydrofuran.

wherein $R^2$ and $R^3$ are as defined above and $R^5$ is lower alkyl on phenyl. The phosphonium salts (IV) are prepared by known methods (e.g., see British Pat. No. 1, 161, 201).

Compounds of formula (II) in which $R^1$ is —CH=CH—(trans) may be prepared by reacting a compound of formula (V) wherein $R^4$ is as defined above with an acrylate ester (VI) wherein $R^6$ is a lower alkyl group (1–4 carbon atoms) in presence of a catalyst consisting of palladium acetate and a triarylphosphine and a tertiary amine such as triethylamine or tributylamine. Optionally, a solvent such as acetonitrile may be used and the reactants may with advantage be heated together in a sealed pressure vessel (e.g., see R. F. Heck et al., *J. Org. Chem.*, 43, 2947 (1978)).

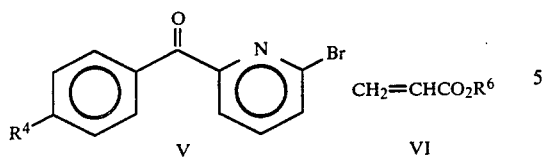

V     VI

Compounds of formula (II) may also be prepared by reacting a compound of formula (VII):

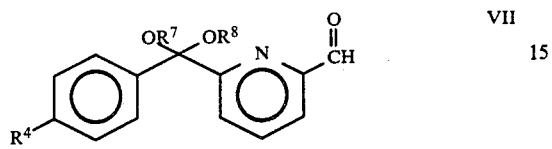

VII wherein $R^7$ and $R^8$ may be the same or different and are lower alkyl, or may together form a cyclic ketal with malonic acid in the presence of a pyridine and piperidine, or with a Wittig reagent prepared by treating a phosphonium salt (VIII A) wherein $R^5$ and $R^6$ are as defined above, m is 1 to 6 or a phosphonate ester (VIII B) wherein $R^6$ is as defined above and $R^9$ is lower alkyl with a suitable base in an appropriate solvent:

$(R^5)_3P^+(CH_2)_mCO_2H$ VIIIA    $(R^6)_3\overset{O}{\overset{\|}{P}}CH_2CO_2R^9$ VIIIB The ketone (II) is generated by acidic hydrolysis of the protecting ketal. The double bond in the group $R_1$ may be reduced if desired with hydrogen in presence of a catalyst such as palladium charcoal.

Compounds of formula (VII) may be prepared from compounds of formula (V) by conversion to a ketal by reaction with a mono or dihydroxy compound in presence of an acid catalyst followed by reaction with a metal alkyl compound for example butyllithium and subsequent treatment with dimethylformamide. The reaction is preferably conducted at low temperature (below −60°) in a solvent such as toluene.

In turn compounds of formula (V) can be prepared by treatment of a compound of formula (IX) wherein X is halogen such as Cl or Br with a metal alkyl compound, for example butyllithium in a suitable solvent such as toluene, followed by reaction with a compound of formula (X) wherein $R^4$ is defined as above.

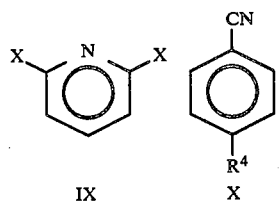

IX     X

2. Compounds of formula (I) may also be synthesized by reacting compounds of formula (XI)

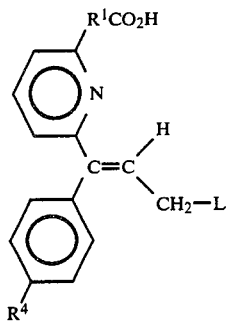

XI wherein $R^1$ and $R^4$ are as defined above and L is a leaving group as defined by J. March, *Advanced Organic Chemistry*, 2nd ed., pages 683 and 895, McGraw Hill, New York, 1977, e.g. Br, Cl, toluene sulphonate, etc. with compounds of formula (XII)

$HNR^2R^3$    XII wherein $R^2$ and $R^3$ are defined for compounds of formula I 3. A further method for synthesis of compound of formula (I) comprises dehydration of compounds of formula (XIII)

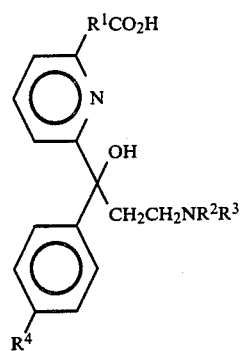

XIII wherein $R^1$, $R^2$, $R^3$ and $R^4$ are as defined above.

Compounds of this invention have the same utilities as antihistamines used clinically at present. They bind competitively to the $H_1$ histamine receptor site and they may be used to relieve symptoms of nasal stuffness due to colds and vasomotor rhinitis and for the symptomatic control of all allergic conditions including nasal allergy, perennial rhinitis, urticaria, angioneurotic oedema, allergic conjunctivitis, food allergy, drug and serum reactions, insect bites and stings and desensitizing reactions. The compounds are also indicated in all conditions responsive to its antipuritic activity including allergic dermatoses, neurodermatitis, anogenital pruritus, and pruritus of non-specific origin such as eczema, and of specific cause such as chickenpox, photosensitivity and sunburn. In contrast to the antihistamines in present use, the compounds of this invention are not sedating and have little or no anticholinergic side effects.

The amount of active compound required for use in the above conditions will vary both with the route of administration, the condition under treatment and the mammal undergoing treatment, and is ultimately at the discretion of the physician. A suitable oral dose of the active compound for a mammal is in the range of from about 0.025 to 1.0 mg per kilogram body weight per day; preferably from 0.04 to 0.24 mg/kg. For example a typical dose for a human recipient of compound A is 0.12 mg/kg body weight per day.

The desired daily dose is preferably presented as from one to six sub-doses administered at appropriate intervals throughout the day as needed. Where three sub-doses of compounds of formula (I) are employed, each will preferably lie in the range of from about 0.014 to 0.08 mg/kg body weight; for example, a typical sub-dose (which can be given in a pharmaceutical formulation such as a tablet, capsule or syrup) for a human recipient is about 2 mg.

While it is possible for the active compound previously described to be administered alone as the raw chemical, it is preferable to present the active compound, a compound of formula (I), as a pharmaceutical formulation. Formulations of the present invention, both for veterinary and for human medical use, comprise the active compound together with one or more pharmaceutically acceptable carriers thereof and optionally any other therapeutic ingredients. For example, the active compound may be formulated with a sympathomimetic agent such as the decongestant pseudoephedrine or phenylpropanolamine, an antitussive such as codeine, an analgesic such as acetaminophen, an antiinflammatory and an antipyretic such as aspirin, or an expectorant such as guaifenesin. The carrier(s) must be pharmaceutically acceptable in the sense of being compatible with the other ingredients of the formulation and not deleterious to the recipient thereof.

The formulations include those suitable for oral, rectal, topical, nasal, ophthalmic or parenteral (including subcutaneous, intramuscular and intravenous) administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into the desired formulations.

Formulations of the present invention suitable for oral administration may be presented as discrete units such as capsules, cachets, tablets or lozenges, each containing a predetermined amount of the active compound (defined herein as a compound of formula (I); as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrat, lubricant, inert diluent, surface active agent or dispersing agent. Molded tablets comprised of a mixture of the powdered active compound with any suitable carrier may be made by molding in a suitable machine.

A syrup may be made by adding the active compound to a concentrated, aqueous solution of a sugar for example sucrose to which may also be added any accessory ingredient(s). Such accessory ingredient(s) may include flavourings, an agent to retard crystallization of the sugar or an agent to increase the solubility of any other ingredient, such as a polyhydric alcohol for example, glycerol or sorbitol, and suitable preservatives.

Formulations for rectal administration may be presented as a suppository with a usual carrier such as cocoa butter, or hydrogenated fats or hydrogenated fatty carboxylic acids.

Formulations suitable for parenteral administration conveniently comprise a sterile aqueous preparation of the active compound which is preferably isotonic with the blood of the recipient.

Nasal spray formulations comprise purified aqueous solutions of the active compound with preservative agents and isotonic agents. Such formulations are adjusted to a pH and isotonic state compatible with the nasal mucous membranes.

Ophthalmic formulations are prepared by a similar method to the nasal spray except the pH and isotonic factors are adjusted to match that of the eye.

Topical formulations comprise the active compound dissolved or suspended in media such as mineral oil, petrolatum, polyhydroxy alcohols or other bases used for topical pharmaceutical formulations. The addition of other accessory ingredients, vide infra, may be desirable.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

When used in medicine, the salts of the compound of formula (I) should be both pharmacologically and pharmaceutically acceptable, but non pharmaceutically acceptable salts may conveniently be used to prepare the free active compound or pharmaceutically acceptable salts thereof and are not excluded from the scope of this invention. Such pharmacologically and pharmaceutically acceptable salts include, but are not limited to, those prepared from the following acids: hydrochloric, hydrobromic, sulfuric, nitric, phosphoric, maleic, salicylic, p-toluenesulfonic, tartaric, citric, methanesulfonic, formic, malonic, succinic, naphthalene-2-sulfonic and benzenesulfonic. Also pharmaceutically acceptable salts can be prepared as alkaline metal or alkaline earth salts, such as sodium, potassium or calcium salts of the carboxylic acid group.

The following Examples are provided by way of illustration of the present invention and should in no way be construed as a limitation thereof. All temperatures indicated are in degrees Celsius.

EXAMPLE 1

3-{6-[3-Pyrrolidino-1-(4-tolyl)prop-1E-enyl]-2-pyridyl} propionic acid

Butyllithium (50 mL, 1.65M in hexane) was added under nitrogen to a stirred suspension of 2,6-dibromopyridine (19.5 g) in dry ether (200 mL) at $-50°$. After 0.75 hr a solution of 4-tolunitrile (10 g) in ether (50 mL) was added; stirring was continued at $-50°$ for 3 hrs. The mixture was allowed to warm to $-30°$ and treated with hydrochloric acid (200 mL, 2M). The precipitated solid was collected, washed with water, and recrystallized from aqueous ethanol. The 2-bromo-6-(4-toluoyl)pyridine formed colourless needles (12.2 g) m.p. $97°-98°$.

A mixture of 2-bromo-6-(4-toluoyl)pyridine (200 g), ethylene glycol (85 mL), p-toluenesulphonic acid (32 g) and benzene (11 mL) was boiled under a Dean/Stark trap until water collection had become very slow (about 20 mL collected in 16 hours).

The cooled solution was poured into ice/water containing sodium carbonate 100 g) with stirring. The benzene layer was separated, washed with water, dried with sodium sulphate and evaporated to about 500 mL. Cooling gave a first crop of 2-(6-bromo-2-pyridyl)-2-(4-tolyl)-1,3-dioxolan (compound 1), m.p. 113°–114° (170 g). Dilution with petroleum ether gave a second crop, m.p. 109°–112° (34 g). The residue after evaporation (31 g) was recycled.

A solution of compound 1, vide supra, (70 g) in dry toluene (800 mL) was added dropwise during 5 hr to a stirred solution of butyllithium (1.6M in hexane, 200 mL) and toluene (200 mL) at −65° to −72° under nitrogen. After a further 30 minutes at −70°, dry dimethylformamide (40 mL) was added during 35 minutes. Stirring continued overnight at −70° to −60°.

Hydrochloric acid (2N, 400 mL) was added, allowing the temperature to rise to about −10°. After 30 minutes, 2N ammonia (ca. 90 mL) was added to pH 7–8. The toluene layer was separated and the aqueous phase was extracted with ether. The combined organic liquids were washed with ice/water, dried (MgSO$_4$) and evaporated in vacuo below 50°. The aldehyde, 2-(6-formyl-2-pyridyl)-2-(4-tolyl)-1,3-dioxolan, (63.9 g) crystallized on keeping at 3°, m.p. 52°–63°.

The aldehyde prepared above (2.5 g) was dissolved in 1,2-dimethoxyethane (10 mL) and added to a solution of the phosphonate carbanion produced from triethyl phosphonoacetate (2 g) and sodium hydride (0.22 g) in the same solvent. The mixture was stirred for two hours, diluted with ether (25 mL) and treated with hydrochloric acid (5 mL, 2M). The organic phase was separated, washed with water, dried, and evaporated. The resulting oil was dissolved in ethanol (20 mL) containing concentrated hydrochloric acid (3 mL) and water (3 mL). After heating on the steam bath for ten minutes, the solution was diluted with ice water, rendered alkaline with sodium bicarbonate solution, and extracted with ether. Evaporation gave (E)-3-[6-(4-toluoyl)-2-pyridyl]acrylic acid which crystallized from cyclohexane in colorless platelets (1 g), m.p. 108°–111°.

Butyllithium (10 mL, 1.64M in hexane) was added under nitrogen to a stirred suspension of triphenyl-2-pyrrolidinoethylphosphonium bromide (7.2 g) in dry toluene (75 mL). After 0.5 hr, (E)-3-[6-(4-toluoyl)-2-pyridyl]acrylic acid, vide supra, (4.8 g) in toluene (50 mL) was added. The suspension, initially orange, became deep purple, then slowly faded to yellow during 2 hours heating at 75°. The cooled solution was diluted with ether (150 mL) and treated with hydrochloric acid (50 mL, 2M). The aqueous phase was separated, washed with ether, and basified with potassium carbonate (ice) and extracted with ether. The mixture of isomeric esters obtained by evaporation was dissolved in ethanol (100 mL) containing sodium hydroxide solution (20 mL, 1M) and partially evaporated on the steam bath under reduced pressure for 5 minutes. The residual aqueous solution was neutralized with sulphuric acid (20 mL, 0.5M) and evaporated to dryness. The solid residue was extracted with hot isopropanol (3×50 mL) and the extracts were concentrated until crystallization commenced. The (E)-3-{6-[3-pyrrolidino-1-(4-tolyl)prop-1E-enyl]-2-pyridyl}acrylic acid (compound 2) after recrystallization from isopropanol, melted at 222° (decomp).

A solution of compound 2, vide supra, (3 g) in alcohol (100 mL) containing Raney nickel (1 g) was stirred under hydrogen at room temperature and pressure until the calculated quantity of hydrogen had been absorbed (ca. 45 minutes). The reduced ester was recovered by filtration and evaporation and purified by column chromatography on silica gel using petroleum ether as eluent. Butyllithium (10 mL, 1.64M in hexane) was added under nitrogen to a stirred suspension of triphenyl-2-pyrrolidinoethylphosphonium bromide (7.2 g) in dry toluene (75 mL) to prepare a Wittig reagent. Treatment of this ester with Wittig reagent by the method of Example 1 followed by saponification gave a mixture of two isomeric acids which were separated by fractional crystallization from ethyl acetate/petroleum ether mixtures. The less soluble E isomer, 3-{6-[3-Pyrrolidino-1-(4-tolyl)prop-1E-enyl]-2-pyridyl}-propionic acid (Compound B), melted at 156°–157°.

EXAMPLE 2

(E)-3-{6-[3-Dimethylamino-1-(4-tolyl)prop-1E-enyl]-2-pyridyl}acrylic acid.

Treatment of (E)-3-[6-(4-toluoyl)-2-pyridyl]acrylic acid, vide supra, with the Wittig reagent derived from triphenyldimethylaminoethylphosphonium bromide by the method of example 1 gave a mixture of isomeric acids which were separated by fractional crystallization from ethyl acetate. The less-soluble E-isomer, (E)-3-{6-[3-dimethylamino-1-(4-tolyl)prop-1E-enyl]-2-pyridyl}acrylic acid was puried by crystallization from isopropanol, m.p. 222°–225° (decomp.)

EXAMPLE 3

The following compounds were synthesized by a method similar to that described for compound 2 in example 1, vide supra,:

(a) (E)-3-{6-[3-Pyrrolidino-1-(4-methoxyphenyl)-prop-1E-enyl]-2-pyridyl}acrylic acid, m.p. 231°–232° (Dec), (b) (E)-3-{6-[1-(4-chlorophenyl)-3-pyrrolidinoprop-1E-enyl]-2-pyridyl}acrylic acid, m.p. 218°–220° (Dec), (c) (E)-3-{6-(1-phenyl-3-pyrrolidinoprop-1E-enyl)2-pyridyl)acrylic acid, m.p. 180°–182° (Dec).

EXAMPLE 4

6-[3-pyrrolidino-1-(4-tolyl)prop-1E-enyl]-pyridine-2-carboxylic acid

A solution of (6-bromo-2-pyridyl)-2-(4-tolyl)-1,3-dioxolan (7 g) in dry toluene (80 mL) was added dropwise under nitrogen to a stirred solution of butyl lithium (1.6M in hexane, 20 mL) cooled below −60°. After three hours at this temperature solid carbon dioxide (25 g) was added. The mixture was allowed to warm to 10°, treated with hydrochloric acid (2M, 20 mL) and filtered from a small quantity of solid (3). The toluene layer was separated and concentrated, leaving an oil (7 g). This was heated on the steam bath for ten minutes with 6M hydrochloric acid (10 mL) containing just sufficient alcohol to give a clear solution. Cooling and dilution with water gave a gummy solid which crystallized from water in colourless needles m.p. 151°–3°. (Treatment of the solid 3 with hydrochloric acid afforded a further 0.9 g of the same material). Esterification of this acid with ethanol/sulphuric acid afforded after the usual work up procedure ethyl 6-(4-tolyl)-pyridine-2-carboxylate (Compound 4) (2.8 g) as a colourless oil which slowly crystallized.

Treatment of compound 4, vide supra, with the Wittig reagent derived from triphenyl-2-pyrrolidinoethylphosphonium bromide by the method of Example I gave, after saponification, a mixture of two geometrical isomers, which were separated by extraction with hot ethyl acetate. The insoluble E-isomer (the title compound), after crystallization from isopropanol, melted at 200°–202°. Cooling of the ethyl acetate solution from Example 3 led to crystallization of the more soluble Z isomer, m.p. 187°–9°.

EXAMPLE 5

Antihistaminic Activity

In vitro antihistiminic activity: The longitudinal muscle was isolated from the intact ileum of guinea-pigs (Hartly, male 250–400 g) and placed in an organ bath under 300 mg tension. After one hour of equilibration, cumulative concentration-response curves (Van Rossum, J. M., *Arch. Int. Pharmacodyn. Ther.* 143, 299–330, 1963) to histamine were obtained. Following washing, the tissues were incubated for one hour with the test compound and then a second histamine concentration-response curve was run. Shifts to the right of the agonist concentration-response curve produced by the antagonists were used to construct Schild plots (Arunlakshana, O. and Schild, H. O., *Br. J. Pharmacol:* 14, 48–58, 1959). Regression of Log (dr-1) on Log [B], where dr is an equiactive response in the presence and absence of antagonist and [B] is the molar concentration of antagonist, allowed an estimate of $pA_2$, i.e. the negative log of the concentration of antagonist which shifts the control histamine concentration-response curve 2X to the right.

TABLE I

| Results of Antihistamine Assays | |
|---|---|
| Compound | $pA_2$ |
| Triprolidine | 10.1 |
| A | 9.2 |
| B | 8.2 |
| C | 8.9 |
| D | 9.0 |
| E | 7.4 |
| F | 8.9 |

EXAMPLE 6

Formulations

| (A)-Injection | |
|---|---|
| Ingredient | Amount per ampoule |
| Compound of formula (I) | 1.0 mg |
| Water for Injections, q.s. | 1.0 mL |

The finely ground active compound is dissolved in the water for Injections. The solution is filtered and sterilized by autoclaving.

| (B)-Suppository | |
|---|---|
| Ingredient | Amount per suppository |
| Compound of Formula (I) | 1.0 mg |
| Cocoa Butter, or Wecobee TM Base q.s. | 2.0 g |

Wecobee is a trademark and is a hydrogenated fatty carboxylic acid.

The finely ground active compound is mixed with the melted suppository base (either Cocoa Butter or Wecobee TM base), poured into molds and allowed to cool to afford the desired suppositories.

| (C)-Syrup | |
|---|---|
| Ingredient | Amount per 5 mL |
| Compound of Formula (I) | 1.0 mg |
| Ethanol | 0.3 mg |
| Sucrose | 2.0 mg |
| Methylparaben | 0.5 mg |
| Sodium Benzoate | 0.5 mg |
| Cherry Flavour | q.s. |
| Coloring | q.s. |
| Water | q.s. to 5.0 mL |

Ethanol, sucrose, sodium benzoate, methylparaben, and flavouring are combined in 70% of the total batch quantity of water. Coloring and the active compound are dissolved in the remaining water, then the two solutions are mixed and clarified by filtration.

| (D)-Tablet | |
|---|---|
| Ingredient | Amount per Tablet |
| Compound of Formula (I) | 1.0 mg |
| Lactose | 110.0 mg |
| Corn Starch, Pregelatinized | 2.5 mg |
| Potato Starch | 12.0 mg |
| Magnesium stearate | 0.5 mg |

The active compound is finely ground and intimately mixed with the powdered excipients lactose, corn starch, potato starch and magnesium stearate. The formulation is then compressed to afford a tablet weighing 126 mg.

| (E)-Capsule | |
|---|---|
| Ingredient | Amount per Capsule |
| Compound of Formula (I) | 1.0 mg |
| Lactose | 440.0 mg |
| Magnesium Stearate | 5.0 |

The finely ground active compound is mixed with the powdered excipients lactose, corn starch and stearic acid and packed into two part, gelatin capsules.

| (F)-Tablet | |
|---|---|
| Ingredient | Amount per Tablet |
| Compound of Formula (I) | 1.0 mg |
| Pseudoephedrine HCl | 60.0 mg |
| Lactose | 62.5 mg |
| Potato Starch | 14.0 mg |
| Magnesium Stearate | 1.0 mg |
| Gelatin | 2.8 mg |

A tablet is prepared from the above formulation by the method previously described in Example 7 (D).

| (G)-Syrup | |
|---|---|
| Ingredient | Amount per 5 mL |
| Compound of Formula (I) | 1.0 mg |
| Pseudoephedrine HCl | 30.0 mg |
| Codeine Phosphate | 10.0 mg |
| Guaifenesin | 100 mg |
| Methylparaben | 0.5 mg |
| Sodium benzoate | 0.5 mg |
| Flavor | q.s. |

(G)-Syrup

| Ingredient | Amount per 5 mL |
| --- | --- |
| Color | q.s. |
| Glycerol | 500 mg |
| Sucrose | 2000 mg |
| Purified Water | q.s. to 5.0 mL |

A syrup containing other active ingredients in addition to a compound of formula (I) is prepared from the above ingredients by an analogous method to that described for Example 7 (C) above.

(H)-Nasal Spray

| Ingredient | Amount per 100.0 mL |
| --- | --- |
| Compound of Formula (I) | 1 g |
| Sodium Chloride | 0.8 g |
| Preservative | 0.5 g |
| Purified Water | q.s. 100.0 mL |

The preservative is dissolved in warm purified water and after cooling to 25°–30° C. the sodium chloride and the compound of formula (I) are added. The pH is then adjusted to 5.5–6.5 and purified water is added to bring the final volume to 100.0 mL.

(I)-Ophthalmic Solution

| Ingredient | Amount per 100.0 mL |
| --- | --- |
| Compound of Formula (I) | 0.1 g |
| Sodium Chloride | 0.8 g |
| Preservative | 0.5 g |
| Water for Injection | q.s. 100.0 mL |

This formulation is prepared in a similar way to the nasal spray.

| Ingredient | Amount per 100.0 mL |
| --- | --- |
| Compound of Formula (I) | 0.1 g |
| Emulsifying Wax, N.F. | 15.0 g |
| Mineral Oil | 5.0 g |

We claim:

1. A compound of formula (I)

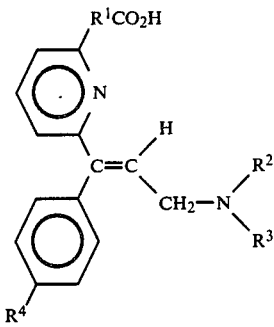

a straight or branched lower alkyl (1–4 carbon atoms) ester, or a pharmaceutically acceptable salt thereof; wherein $R^1$ is $(CH_2)_n$, n is an integer 1–7, or $R^2$ and $R^3$ are the same or different and are hydrogen, $C_{1-4}$ alkyl or taken together with the nitrogen to which they are attached form a azacyclobutane, pyrrolidine or piperdine ring; $R^4$ is hydrogen, halogen, $C_{1-4}$ alkoxy or $C_{1-4}$ alkoxy or $C_{1-4}$ alkyl optionally substituted by one to three halogen atoms.

2. 3-{6-[3-Pyrrolidino-1-(4-tolyl)prop-1E-enyl]-2-pyridyl}propionic acid.

3. A pharmaceutically acceptable salt of 3-{6-[3-Pyrrolidino-1-(4-tolyl)prop-1E-enyl]-2-propionic acid.

4. The hydrochloride salt of claim 3.

5. A method of providing an antihistiminic effect in a mammal in need thereof comprising administering to said mammal an effective antihistimatic amount of the compound of formula (I),

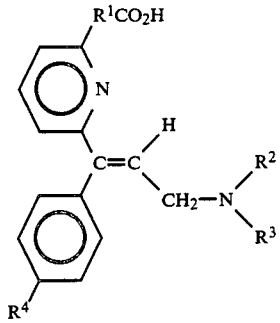

or a pharmaceutically acceptable salt thereof; wherein $R^1$ is $(CH_2)_n$, n is an integer 1–7; $R^2$ and $R^3$ are the same or different and are hydrogen, $C_{1-4}$ alkyl or taken together with the nitrogen to which they are attached form a azayclobutane, pyrrolidine, or piperdine ring; $R^4$ is hydrogen, $C_{1-4}$ alkoxy or $C_{1-4}$ alkyl optionally substituted by one to three halogen atoms.

6. A method of obtaining an antihistiminic effect in a mammal in need thereof comprising administering of an effective antihistiminic amount of the compound of claim 2 to said mammal.

7. A method of obtaining an antihistiminic effect in a mammal in need thereof comprising administering of an effective antihistiminic amount of claim 3 to said mammal.

* * * * *